United States Patent [19]
Liu

[11] Patent Number: 6,020,207
[45] Date of Patent: Feb. 1, 2000

[54] OPTICAL ANALYSIS TECHNIQUE AND SENSORS FOR USE THEREIN

[75] Inventor: Su Yi Liu, Sarasota, Fla.

[73] Assignee: World Precision Instruments, Inc., Sarasota, Fla.

[21] Appl. No.: 09/098,859

[22] Filed: Jun. 17, 1998

[51] Int. Cl.[7] .......................... G01N 21/63; G01N 21/64; G01N 21/65
[52] U.S. Cl. ...................... 436/164; 436/172; 422/82.08; 422/82.09; 422/82.11
[58] Field of Search ..................... 436/164, 172; 422/82.08, 82.09, 82.11, 82.05; 385/142–145, 12

[56] References Cited

U.S. PATENT DOCUMENTS

| | | |
|---|---|---|
| 3,819,250 | 6/1974 | Kibler . |
| 3,894,788 | 7/1975 | Gambling et al. . |
| 3,995,934 | 12/1976 | Nath . |
| 3,998,591 | 12/1976 | Eckfeldt . |
| 4,045,119 | 8/1977 | Eastgate . |
| 4,690,560 | 9/1987 | Coogan . |
| 4,763,009 | 8/1988 | Fevrier et al. ........................ 250/458.1 |
| 5,030,010 | 7/1991 | Birkle . |
| 5,134,445 | 7/1992 | Toge . |
| 5,165,773 | 11/1992 | Nath . |
| 5,221,387 | 6/1993 | Robbins et al. . |
| 5,267,341 | 11/1993 | Shearin . |
| 5,304,171 | 4/1994 | Gregory et al. . |
| 5,340,715 | 8/1994 | Slovacek et al. ........................... 435/6 |
| 5,444,807 | 8/1995 | Liu . |
| 5,485,270 | 1/1996 | Freud et al. . |
| 5,570,447 | 10/1996 | Liu . |
| 5,604,587 | 2/1997 | Che et al. . |
| 5,738,992 | 4/1998 | Cook et al. ................................. 435/6 |
| 5,751,415 | 5/1998 | Smith et al. ............................ 356/301 |

FOREIGN PATENT DOCUMENTS 57-30802  2/1982  Japan .

*Primary Examiner*—Jeffrey Snay
*Attorney, Agent, or Firm*—Alix, Yale & Ristas, LLP

[57] ABSTRACT

The detection of a chemical specie of interest is accomplished by immobilizing sensing molecules on the inner wall of a liquid core optical waveguide, the waveguide comprising a capillary tube and the sensing molecules being selected to interact with the specie of interest carried by the liquid which forms the waveguide core. The interaction produces a change in an optical characteristic of the waveguide which may be detected by illuminating the waveguide with analysis light.

20 Claims, 4 Drawing Sheets

OPTICAL ANALYSIS TECHNIQUE AND SENSORS FOR USE THEREIN

BACKGROUND OF THE INVENTION

(1) Field of the Invention

This invention relates to the optical detection of chemical species which are dissolved in solution and, particularly, to sensor cells for use in such detection. More specifically, this invention is directed to improvements in the optical identification of ion species, molecular species, antigens, antibodies, DNA and RNA, as well as the determination of their concentrations, and especially to liquid waveguide capillary cells which, when employed as sensors, permit such improvements to be achieved. Accordingly, the general objects of the present invention are to achieve novel and improved methods and apparatus of such character.

(2) Description of the Prior Art

There are two principal classes of chemical sensor based on the use of fiber optics. In a first of these classes of chemical sensor, sensing molecules, such as color indicating dyes, are immobilized at the distal end of a solid optical fiber. The response of the immobilized sensing molecules to an analyte in solution may be measured either by light absorption or fluorescent light spectroscopy. Sensors of this type are characterized by low sensitivity and slow response time. In order to increase the intensity of the signal of interest to a practical level, when the detection modality is absorption, a high concentration of color indicator would have to be immobilized in a very limited surface area. A high concentration of the dye, however, has a buffering effect upon the analyte thus slowing response time. In addition, loading a high concentration of dye in a small area is technically difficult because it is desirable that all of the sensing dye molecules be in contact with the fluid analyte without being leached away. If the dye capture "structure" is made very permeable to the analyte molecules to maximize such contact, then the color indicator either cannot be loaded in high concentration or it will leach out easily. Conversely, if the capture "structure" is designed to prevent indicator molecules from leaching out, normally the analyte cannot quickly penetrate such structure and react with the dye.

In the second class of sensor, known in the art as evanescent sensors, light transmitted through a solid optical fiber "leaks" to the fiber's exterior surface. The sensor normally has a single layer of sensing material applied to the exterior of the fiber optic for direct exposure to a sample solution. This single layer coating allows for intimate interaction between sensing molecules and analyte molecules in the sample solution. Evanescent sensors, while having a fast response time, are characterized by limited sensitivity.

For many applications, a sensor configured as a flow cell is preferred because a flow cell provides a sensing environment in which mechanical structure, ambient light, temperature, sample exchange rate and sample volume may be accurately controlled. For a sensor of the types described above to be installed inside a flow cell, the cell must obviously be larger than the sensor. Thus, an evanescent wave sensor would be normally inserted axially inside of flow cell defining tubing. Since evanescent wave sensors are normally composed of stripped silica fibers which are fragile, the requisite liquid tight seal between the fiber and the flow cell tubing is difficult to achieve.

A unique sensor based upon use of a liquid waveguide capillary as a flow cell, hereinafter a "LWCC" is described In U.S. Pat. No. 5,570,447. In an LWCC a capillary tube comprised of glass, quartz, silica or a suitable polymer which has been exteriorly coated with a low refractive index material acts as a fiber optic when filled with most fluids.

SUMMARY OF THE INVENTION

The present invention overcomes the above-briefly discussed and other deficiencies and disadvantages of the prior art and, in so doing, provides optical analysis techniques characterized by enhanced sensitivity, reduced complexity and improved capability to identify ion species, molecular species, antigens, antibodies, DNA and RNA. To implement the present invention, "sensing" molecules are coated, i.e., immobilized, upon the inner wall surface of a LWCC to thereby define a novel sensor cell. When a solution containing the appropriate analyte flows into the cell, the analyte interacts with the immobilized sensing molecules. When analysis light is subsequently transmitted through the internally coated LWCC, optical signals indicative of this interaction can be collected and analyzed. Such collection may, for example, be accomplished with an optical fiber positioned at an end of the cell.

In the practice of the present invention, several different analysis methodologies may be employed, including light absorption, fluorescence and Raman spectroscopy. A meaningful and detectable optical signal may be generated by the interaction of the immobilized sensing molecules with the analyte or such a signal may be induced by the interaction of the immobilized sensing molecules with the fluid contents of the cell. A LWCC in accordance with the invention is characterized by the important advantage of having a large wall surface area to cell volume ratio. This large ratio allows more sensing molecules to be immobilized for a given volume of sample fluid than would otherwise be possible. The response time of apparatus employing the invention is rapid because only a single layer of sensing molecules is involved. Thus, the combination of an LWCC and a wall deposited layer of sensor molecules in accordance with the invention yields enhanced detection sensitivity and speed when compared to the prior art.

BRIEF DESCRIPTION OF THE DRAWINGS

The present invention may be better understood, and its numerous objects and advantages will become apparent to those skilled in the art, by reference to the accompanying drawings wherein like reference numerals refer to like elements in the several figures, and wherein.

DETAILED DESCRIPTION OF THE DISCLOSED EMBODIMENTS

Figure 1:
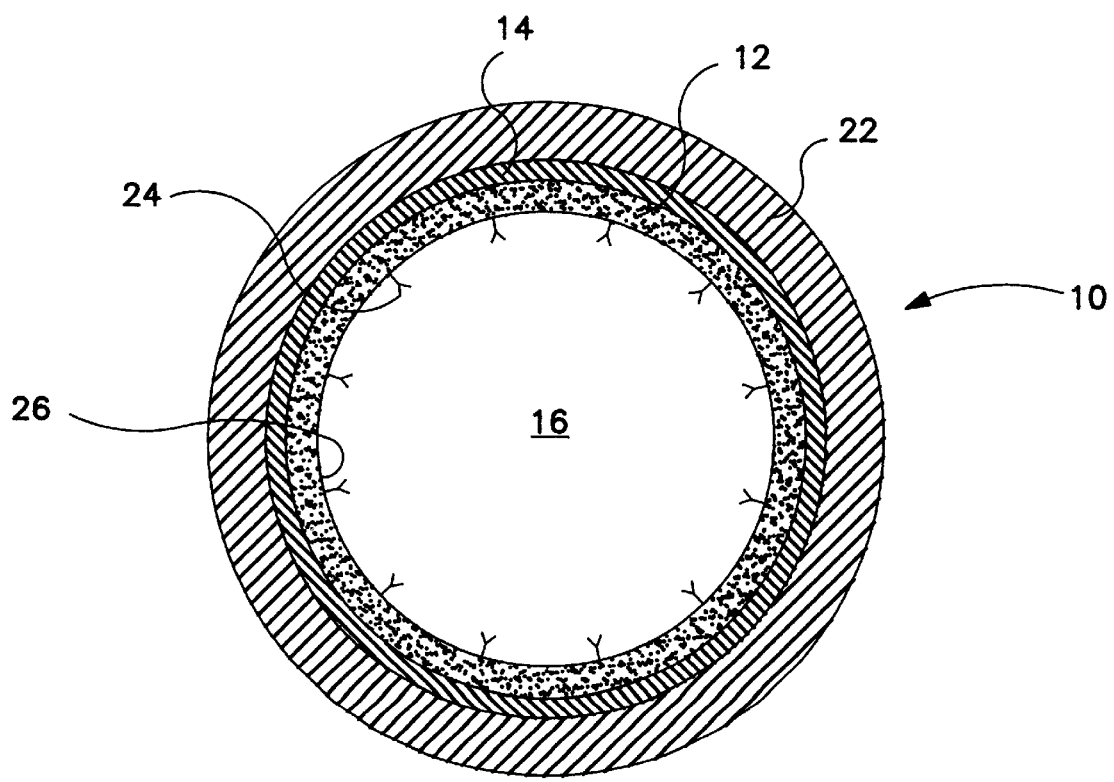
FIG. 1 is a schematic, cross-sectional, front elevational view of a sensor cell in accordance with the invention.

A liquid core waveguide sensor cell in accordance with the invention is shown in cross-section, and indicated generally at 10, in FIG. 1. Sensor cell 10 comprises a capillary, i.e., a tube, 12 of optically transparent material coated on its exterior surface with an amorphous polymer material 14 having a refractive index which is lower than that of the core liquids to be employed, i.e., the liquids which will fill the inside of the capillary. The refractive index of the coating will desirably be less than 1.33 so that the core liquid of the LWCC may be an aqueous solution. A preferred coating material is the copolymer of 2,2 bis-trifluoromethyl-4,5 difluoro-1,3 dioxole (PDD) with tetrafluoroethylene (TFE). This coating material is commercially available as "Teflon AF". The coating 14 will preferably have a thickness which is at least four (4) times the wavelength of the analysis light to be employed.

Figure 3:
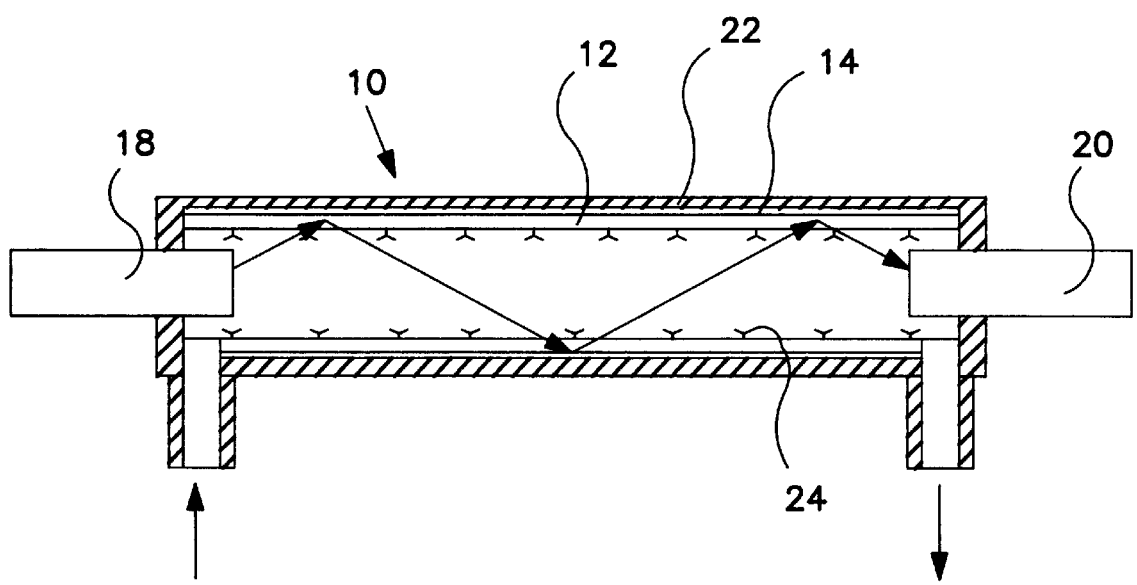
FIG. 3 is a cross-sectional, schematic, side elevation view of apparatus for use in the practice of the invention, the FIG. 3 apparatus employing the sensor cell of FIGS. 1 and 2.
Figure 4:
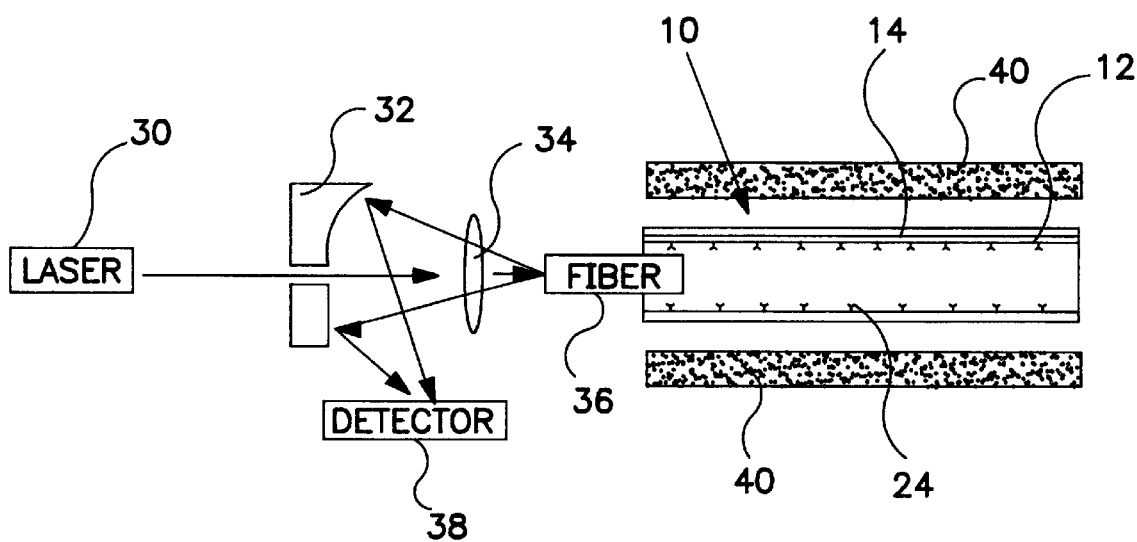
FIG. 4 is a cross-sectional view, similar to FIG. 3, which schematically shows alternative apparatus for use in the practice of the novel techniques of the invention.

Analysis light launched into the liquid core 16 of waveguide 10, for example in the manner depicted in FIGS. 3 and 4, behaves in most respects as it would in a solid core optical fiber. FIG. 3 displays one method by which light can be conveniently launched into the liquid core 16 of the cell. In the FIG. 3 embodiment, solid optical fibers 18 and 20, inserted incrementally into the core fluid respectively at the proximal and distal ends of tube 12, are respectively used as input and output light conduits as schematically represented by a single hypothetical light ray (arrows). It will be recognized by those skilled in the art that the analysis light will be injected into the waveguide in such a manner as to be within the acceptance angle of the waveguide, i.e., the LWCC.

The capillary tubing 12 will have a refractive index which is equal to or greater than the refractive index of the core liquid. Tubing 12 may be an inorganic material such as fused silica, quartz or glass, or may be a clear plastic such as PMMA, polystyrene or similar polymers that are presently used, for example, to make clear plastic solid optical fibers. The cell 10 will typically be provided with a protective outer cover 22.

Figure 2:
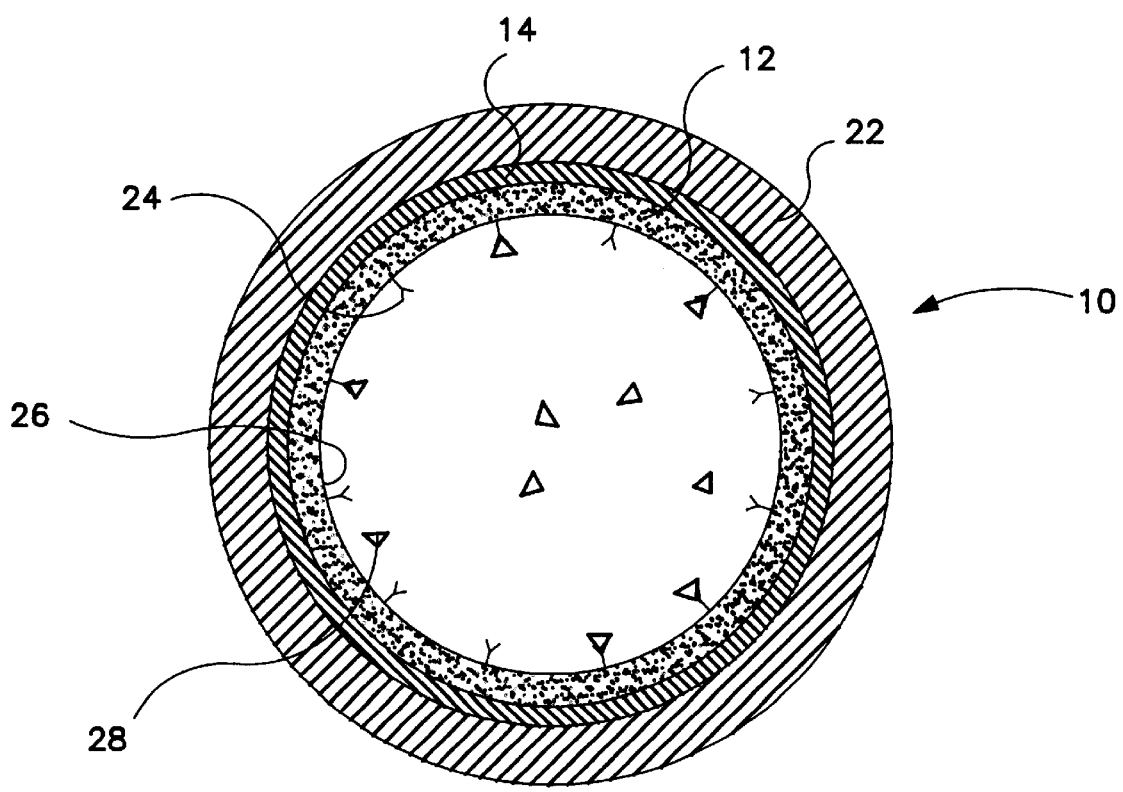
FIG. 2 is a view, similar to FIG. 1 which represents the operation of the sensor cell during practice of the invention.

In accordance with the invention, as best seen from FIGS. 1 and 2, "sensing" molecules 24 are immobilized on the interior wall surface 26 of capillary 12. Sensing molecules usually are more easily immobilized on plastic surfaces than on inorganic materials. Plastic capillaries are also more flexible than comparable glass or quartz capillaries. However, the less flexible capillary defining materials, such as quartz, have better light transmission properties and are more stable when compared to the plastic tubes.

In the practice of the invention, an extremely broad range of sensing molecules can be used as photometric indicators. The major requirements for successful chemical and biochemical indicators are: (1) the ability of the indicator, i.e., the sensing molecules, to be immobilized on the inside wall surface of the tubing and (2) the ability of the analyte in the liquid core and the indicator molecules to interact to produce, when excited by light transmitted through the liquid core, a detectable optical signal through light absorption, fluorescence or Raman spectra. In FIG. 2, the analyte molecules are schematically indicated at 28 and, as noted above, the indicator (sensing) molecules are indicated at 24.

In the context of this invention, the indicator material, i.e., the immobilized sensing molecules, can be classified into three types. In the first type, a sensing molecule produces an optical signal itself when interacting with a specific analyte in a solution. A pH indicator dye is an example of an indicator material of the first type. The color of the indicator dye, an absorbance measure, or the magnitude of its fluorescence intensity, will depend on the proton concentration of the fluid in the core region of the cell. A second type of sensing molecule can catalyze a chemical reaction in the cell core fluid so as to cause some of the molecules in the solution to change their optical properties. An enzyme molecule is an example of such a second type of sensing material. Enzymes, when properly immobilized on the inner surface 26 of the tubing so that enzyme activity is preserved, can catalyze chemical reactions resulting in detectable optical signals. A third type of sensing molecule selectively attracts other molecules from a sample fluid to the inner wall surface 26 of the cell. The thus attracted and retained molecules can then be detected by their own absorbance or fluorescence. An antigen exemplifies this third type of sensing material. After antibodies in the fluid sample have been allowed to bond with the immobilized antigens on the inner wall surface, clean buffer solution may be used to flush out the remaining sample fluid. The bound antibodies can then be detected directly by, for example, measuring light absorption at 280 nm.

The above briefly-discussed detection modalities will now be described in more detail.

Absorbance

Sensors based on absorption spectroscopy are economical and reliable. However, the relatively low sensitivity of prior art absorption spectroscopy has severely limited the utility of this detection method. When combined with the present invention, absorption spectroscopy yields exceptional sensitivity because of the large surface area available for immobilizing chromophores when compared to the diameter of the analysis light beam. For example, a 0.4 mm ID waveguide sensor with a length of one (1) meter long has an internal surface area available to immobilize chromophores in the light beam path which is about 10,000 times the cross sectional area of the light beam. This is equivalent to a light path through 5,000 stacked thin glass sheets, each sheet being coated on both surfaces with immobilized chromophore. If N is the number of molecules immobilized on each square nanometer of the inner wall surface 26 of a sensor cell in accordance with the invention, and employing N instead of molar concentration C, Beer's law may be restated as follows:

$$A = 3.32 \times 10^{-7} e\, N\, L/R \quad (A)$$

where e is the molar extinction coefficient, R the inner radius of the capillary tubing and L its length in millimeters. Clearly, N and the L/R ratio are significant factors determining the magnitude of the absorbance A and, accordingly, are important indices of the ultimate sensitivity of the sensor.

Equation (A) provides a convenient tool for estimating the sensitivity of liquid core waveguide absorption spectroscopy sensors in accordance with the invention. Estimating the sensitivity of a pH sensor can be used as an illustrative example. One way to covalently link a specially modified pH dye to a silica surface is first to treat, i.e., silanize, the silica surface with an amine terminated silane. The pH dye may be a commercially available dye which has been modified with a functional group that will form a covalent bond with amine. For example, pH dyes with functioning groups consisting of isothiocyanate, succinimidyl eater, sulfonyl chloride or aldehyde can be employed. It is estimated that there are 4 to 12 hydroxyl groups on each square nanometer of silica surface that can be silanized. On the other hand, many synthetic dye molecules are at least 1 to 10 square nanometers in size. Therefore, the size of the dye molecule becomes a limiting factor that determines how many dye molecules can be immobilized on each square nanometer of sensor surface. Assuming that 0.2 molecule of dye is immobilized on each square nanometer, i.e., that there is 1 dye molecule per 5 square nanometers of LWCC surface, and further assuming that the extinction coefficient is 70,000 M cm$^{-1}$, the absorption of a 1 meter long 400 micron ID capillary tube would be 23 absorbance units (AU). If a change of one pH unit in the sample fluid can reduce the absorption by 50% and the spectrometer has a 0.001 AU resolution, the projected sensitivity of the sensor would be 0.00009 pH units. Clearly, for this illustrative case, even a one tenth of a meter long waveguide cell would still yield an excellent pH sensitivity.

Beer's law can also be rewritten to express absorption in terms of nanograms of protein W immobilized on each square millimeter of sensor surface as follows:

$$A = 2 \times 10^{-4} E_{280} W L/R \qquad (B)$$

where $E_{280}$ is extinction coefficient of 0.1%, protein solution at 280 nm. Equation (B) is especially useful for the design of an immunosensor. For immunoglobulin G (IgG), the $E_{280}$ is approximately 1.4 at 280 mn. Normally, 1.0 ng/mm$^2$ (nanograms per square mm) of antibody (IgG) can be immobilized on a silica surface. If the antigen is also an immunoglobuline G of a different species, a maximum of 0.4ng/mm$^2$ can be bound to the antibodies on the silica surface. For an aqueous waveguide 1 meter long with an ID of 400 microns, accordingly, the 280 nm absorbance of the antigen will be about 0.56 absorbance units (AU) when all active antibody binding sites are filled.

Fluorescence

For fluorescence measurements, a liquid waveguide capillary cell (LWCC) sensor may be constructed as shown in FIG. 4. A light source 30, which can be a laser or other collimated light source, illuminates the LWCC 10 via a slit in a mirror 32 and is focused with a lens 34 upon an optical fiber 36 inserted into the LWCC opening. Resulting fluorescent light in the LWCC is scattered both along the LWCC interior waveguide and transversely scattered through the walls of the capillary. The stimulated fluorescent light emission can be collected by either or both of two methods. Firstly, fluorescent light can exit the LWCC via the fiber optic 36 and lens 34 and be focused by the mirror 32 upon a light detector 38 such as a photodiode, photomultiplier or spectrophotometer. This measurement method may be aided by locating a mirror, not shown, at the end of tube 12 which is opposite to fiber 36. Alternatively, or additionally, fluorescent light scattered external to the core may be measured by laterally disposed planar photodiode arrays 40 which can collect most of the scattered fluorescent light. One of the photodiode arrays 40 may be replaced by a suitably shaped mirror. When the photodiode array(s) are employed, the protective cover 22 will be partially or totally eliminated.

An LWCC enhances fluorescence light emission signals by integrating the fluorescence signal along the entire length of the cell. Thus, the LWCC 10 will increase the fluorescent signal more than 100 times for each meter length of LWCC when compared to previous solid fiber sensor probes.

Practical liquid core waveguide sensors can be built with cell lengths of one meter or more. This may be contrasted with typical prior art silica core evanescent sensors which are usually less than 10 cm in length. Thus, for the same surface area of immobilized sensing molecules, the volume of sample fluid required is much less for the LWCC sensor with increased sensitivity.

Raman Light

Raman spectroscopy can provide substantial information about the nature of molecules present in a fluid sample. However, since Raman light scattering usually results in a weak signal, this technique has mostly been used for analyzing concentrated chemical solutions. It is difficult to measure low analyte concentrations using presently available Raman spectroscopy apparatus and techniques. Enhancement of the sensitivity of Raman analysis by the use of a liquid core waveguide was first taught by U.S. Pat. No. 3,770,350 and significant improvements in the technology are disclosed in U.S. Pat. No. 5,604,587. For Raman measurements, the liquid waveguide capillary cell (LWCC) sensor of FIG. 4 may be utilized. Similar in methodology to fluorescent signal processing using a liquid filled waveguide, as discussed above, Raman scattered light is integrated along the length of the sensor cell. Prior art Raman sensors cannot easily be compared directly with the LWCC devices of the present invention. However, in a simple experiment it was determined that for pure or highly concentrated fluid, the liquid core waveguide increased the intensity of the Raman spectrum at least 50 to 100 times for each meter of capillary length depending on the excitation wavelength used. Measurement of the Raman spectrum of a single molecular layer coated on the surface of silica by means of prior art apparatus is not possible because the resulting Raman signal is too weak. The present invention can enhance the Raman signal by at least four orders of magnitude, making it possible to produce Raman spectra in cases which have not previously been feasible.

Experimental Examples (1) A pH Sensor:

A 10 cm length of 550 $\mu$m ID quartz LWCC tubing was first silanized with 2% aminopropyltriethoxysilane (APTS) in water for two hours. A 1 mg/ml concentration of the succinimidyl ester of carboxyfluorescein (FAM) in 100 mM NaHCO$_3$ (pH 8.3) was then introduced into the tubing and incubated for two hours. An estimated 0.15 molecules per square nanometer (nm$^2$) of the carboxyfluorescein (FAM), a pH indicator, became bound to, i.e., formed an immobilized layer on, the interior wall surface 26 of the silanized silica capillary. Changing the pH of the core liquid sample from 4 to 8.3 produced an 0.4 AU absorbance signal change at 495 nm. Only 24 microliters of sample was required and the response time was less than 100 ms. Thus, the sensor had the advantage of high sensitivity, small sample volume and very fast response time. Fluorescence detection could also have been used.

In another example of a pH sensor in accordance with the invention, the capillary was a polystyrene tube having an external coating of TEFLON AF. The inner surface of the polystyrene tube was first treated with a mixture of nitric acid and sulfuric acid to yield a nitrated polymer derivative. This polymer derivative was subsequently reduced to amine with sodium hydrosulfite. A 1 mg/ml concentration of succinimidyl esters of carboxyfluorescein (FAM) was then introduced into the tubing and incubated for one hour. An estimated 0.15 molecules per square nanometer of FAM became linked to the interior surface of the polystyrene tubing. For a sensor having a length of 10 cm and an ID of 0.55 mm, a change in the sample pH from 5 to 7 produced a 0.8 AU absorbance signal change at 495 nm. Only 24 microliters of sample was required and the response time of the sensor was less than 100 ms.

Other cation indicators, such as for calcium, magnesium, lithium, potassium and sodium are available. These additional indicators can also be attached to the surface of a LWCC wall by absorption or by covalent linking. When sample fluid is then introduced into the core region of the sensor cell, the immobilized indicators will cause changes in light absorption and/or fluorescence properties. The optical changes exhibit a quantitative relationship to the amount of analyte in the liquid and can thus be used as a measure of the analyte concentration.

(2) An Immunosensor

A layer of goat anti-rabbit IgG antibody was immobilized on the silanized inner wall surface 26 of a quartz LWCC by covalent bonding. This was accomplished by first exposing the LWCC to 2% of 3-Mercaptopropyltrimethoxysilane (MTS) in dry toluene for one hour. 2 mM of GMBS (a heterobifunctional cross-linker) in absolute ethanol was then introduced into the tubing and incubated for one hour. After rinsing with phosphate buffer solution (PBS), a 1 mg/ml concentration of goat anti-rabbit IgG antibody in PBS was introduced into the tube and incubated overnight. About 1 ng of antibody per square mm of silica surface could be attached to the LWCC wall. While some of the attached antibody lost its binding activity, at least one third of the applied antibody remained functional. To perform the assay, a sample containing 150 mg/ml of rabbit IgG-FITC antigen was pumped into the core region of the sensor cell over a period of ten (10) min. The cell was then flushed with a clean phosphate buffer solution. Since the IgG antigen absorbs light at 280 nm, it was possible to directly measure the amount of antigen which had become bound to the antibody using light absorption. One hundred (100) ng/ml of rabbit IgG antigen was easily detected by direct absorption spectroscopy in a LWCC having a length of 50 cm. Direct detection is an important advantage of using the absorption method, i.e., the test procedure is relatively simple because secondary labeling is not required.

(3) DNA or RNA Sensor for the Diagnosis of Genetic Diseases

The sensor cell had an immobilized layer of oligonucleotides on the inner wall surface of the LWCC. These oligonucleotides had the ability, in turn, to bond to single strands of DNA or RNA containing complementary oligonucleotides. The bound DNA or RNA may be detected using light absorbance at a wavelength of 260 nm or by using fluorescent labeling methods specifically developed for double stranded oligonucleotides. The procedure was as follows:

Biotin, a vitamin present in tissue and blood, was immobilized on the inner surface of a quartz capillary by covalent bonding. Avidin, a glycoprotein present in egg white, was then bound to the immobilized biotin. The avidin thus became an immobilized linker with one site bonding to the LWCC wall via the biotin and other sites being available for bonding to biotinylated oligonucleotides by overnight incubation. Thus, sensor cells comprising LWCCS containing oligonucleotides could be hybridized, i.e., packaged, for future use. Such DNA sensor cells are believed to have utility in detecting genetic disease and cancers because the immobilized single strand oligonucleotide (small segment of DNA or RNA) contains a complementary copy of the DNA or RNA section that represents the finger print of the condition of interest. Thus, when a sample from a subject is introduced into the LWCC, the subject's DNA will combine with the immobilized oligonucleotide if the subject's DNA contains the complementary section of the immobilized oligonucleotide (all the DNA and RNA in the sample have been broken down to single strands before use). The bound DNA or RNA could be measured either by light absorbance at 260 nm or by fluorescence using special hybrid DNA fluorescent indicators.

(4) Sensors based on Enzymatic Reaction

An example of this type of sensor used an immobilized enzyme to cause ammonia to react with a substrate in the reagent. The reaction involves a color change of an indicator in the reagent that can be used to quantify the amount of ammonia in the sample:

Glutamate dehydrogenase (GLDH), an enzyme that can induce a reductive amination, was covalently immobilized on the surface of a 10 cm long LWCC having an ID of 0.55 mm. To determine the concentration of ammonia in a sample, the sample was mixed with an ammonia reagent containing oxoglutarate and NADPH. The mixture was then introduced into the LWCC. The enzyme GLDH causes the analyte (ammonia) to react with the substrate, oxoglutarate, in the mixture. The reaction will transform the color of the NADPH indicator into the colorless reagent NADP. The concentration of the analyte can be determined by the intensity of the color change at 340 nm after a 20 minute incubation.

To summarize the above, the present invention encompass novel and improved optical detection techniques wherein a liquid core waveguide capillary cell functions as either an efficient ion and molecular sensor, an enzyme activated sensor or an immunosensor. The invention is of particular importance in the case of immunoassay techniques. Almost all immunological detection methods currently used depend upon labelling, i.e., a fluorescence, radioisotope or enzyme label must be attached to either the antibody, antigen or a second antibody. The availability of label-free immunoassays would reduce assay time, simplify procedure and reduce cost. To date, a variety of methods have been explored for direct detection of a binding interaction, such methods including potentiometric, piezoelectric, capacitance, surface plasmon resonance and microrefractometry. None of these methods, however, provides "spectral" information that allows identification of a molecule of interest. Indeed, it is often difficult to differentiate the binding signals from interference. Further, most of the previously attempted methods are sensitive to environmental changes such as variations in temperature or in the refractive index of the solution. The present invention permits label-free detection of antibody/antigen bonding through the use of absorption spectroscopy, a detection technique which is economical, reliable and less susceptible to interference from temperature or refractive index changes than other analytical optical techniques. This improved results precipitated by the present invention are attributable, in part, to the fact that an LWCC has much better transmission of light at 280 nm when compared to other techniques and, additionally, to the large wall surface area to beam size ratio of an LWCC which allows sufficient antibody to be immobilized.

While preferred embodiments of the present invention have been illustrated and described in detail, many modifications and changes thereto are within the skill of ordinary artisans. Therefore, the appended claims are intended to cover any and all modifications which fall within the spirit and scope of the invention and, hence, are not limited to the embodiments expressly described above.

What is claimed is:

1. A method for the optical detection of chemical species comprising the steps of:

immobilizing indicator molecules on the inner wall of a capillary tube comprised of an optically clear material, the capillary tube having an interior wall which defines an open core region, the capillary tube further having an intimate exterior coating of an amorphous polymer, the polymer having a refractive index of less than 1.33;

filling the core region of the capillary tube with a liquid having an index of refraction which is greater than that of the coating, the filled tube thus defining a liquid core optical waveguide, the liquid containing an analyte which interacts with the immobilized indicator molecules, the result of the interaction being a modification of an optical characteristic of the waveguide;

illuminating the waveguide core region with analysis light subsequent to the interaction between the indicator molecules and the analyte;

collecting light emanating from the illuminated waveguide; and analyzing the collected light for the occurrence of said optical characteristic modification.

2. The method of claim 1 wherein the step of immobilizing includes:

treating the inner wall of the capillary to enhance the bonding of the indicator molecules thereto.

3. The method of claim 1 wherein the interaction results in a change in the absorbance of the analysis light.

4. The method of claim 1 wherein the interaction results in a change in an optical characteristic of the core liquid.

5. The method of claim 1 wherein the immobilized indicator molecules define a coating on the waveguide interior wall and the interaction results in a change in the fluorescence properties of the internal coating of the waveguide.

6. The method of claim 1 wherein the immobilized indicator molecules define a coating on the waveguide interior wall and the interaction results in a change in the color of the internal coating of the waveguide.

7. The method of claim 1 wherein the immobilized molecules at least in part define a coating on the waveguide interior wall and the interaction comprises the binding of molecules in the core liquid to the immobilized indicate molecules whereby an optical characteristic of the interior wall coating will change.

8. The method of claim 1 wherein the interaction results in a change in the Raman spectrum of the waveguide.

9. The method of claim 2 wherein the interaction results in a change in the absorbance of the analysis light.

10. The method of claim 9 wherein the immobilized indicator molecules define a coating on the interior wall of the waveguide and the change in absorbance occurs in the interior wall coating.

11. The method of claim 10 wherein the change in interior wall coating absorbance results from the binding of molecules in the core liquid to immobilized indicator molecules.

12. A method for the optical detection of chemical species comprising the steps of:

forming a film on the inner wall of a liquid core optical waveguide, the waveguide including a capillary tube comprised of an optically clear material, the capillary tube having an intimate exterior coating of an amorphous polymer, said polymer having a refractive index of less than 1.33, the waveguide inner wall defining an open axial core region of the capillary tube;

filling the core region of the capillary tube with a liquid having an index of refraction which is greater than that of the coating;

illuminating the filled waveguide core region with analysis light;

collecting light emanating from the illuminated waveguide; and analyzing the collected light to determine a characteristic of the coating material.

13. The method of claim 12 wherein the step of analyzing comprises measuring the absorbance of the analysis light.

14. The method of claim 13 wherein the measuring of light absorbance comprises determining a change in absorbance resulting from interaction between molecules of the formed film and an analyte in the liquid with which the core region was filled.

15. A sensor cell for use in the optical detection of a chemical specie of interest comprising:

a capillary tube comprised of an optically clear material, said tube having an axial open core region defined by an inner wall, said tube also having an outer wall which is substantially coaxial with said inner wall;

a coating of an amorphous polymer having a refractive index of less than 1.33 on said tube outer wall, said coating being in intimate contact with said outer wall; and indicator molecules immobilized on said tube inner wall whereby analysis light launched into a liquid disposed in said tube core region will be guided along said tube by reflection from said outer wall coating and will thereby pass through said indicator molecules.

16. The sensor cell of claim 15 wherein said tube inner wall is chemically treated to enhance the bonding of indicator molecules thereto.

17. The sensor cell of claim 15 wherein said indicator molecules define a coating on said tube inner wall and are selected for their ability to interact with a chemical specie of interest in a carrier liquid having an index of refraction which is greater than said outer wall coating whereby, when said tube core region is filled with the carrier liquid, an interaction will occur which changes an optical characteristic of the sensor cell.

18. The sensor cell of claim 17 wherein said tube inner wall is chemically treated to enhance the bonding of indicator molecules thereto.

19. The sensor cell of claim 18 wherein said indicator molecule is selected to interact with the specie of interest to produce, when excited by analysis light, a detectable optical signal comprising at least one of a change in light absorbance, a change in fluorescence or a change in the Raman spectra of the liquid filled tube.

20. The sensor cell of claim 19 wherein said tube is comprised of fused silica, quartz, glass or a clear plastic.

* * * * *